United States Patent
Sommermeyer et al.

(10) Patent No.: US 7,041,175 B1
(45) Date of Patent: May 9, 2006

(54) METHOD FOR THE CONTINUOUS PRODUCTION OF HYDROLYTICALLY BROKEN DOWN AND POSSIBLY SUBSTITUTED STARCH, USE OF HYDROLYTICALLY BROKEN DOWN STARCH AND DEVICE FOR PRODUCING SAME

(75) Inventors: Klaus Sommermeyer, Deutschland (DE); Klaus Henning, Deutschland (DE); Michael Gorg, Deutschland (DE); Thomas Maul, Deutschland (DE)

(73) Assignee: Fresenius AG, Bad Homburg (DE)

( * ) Notice: Subject to any disclaimer, the term of this patent is extended or adjusted under 35 U.S.C. 154(b) by 0 days.

(21) Appl. No.: 09/485,377

(22) PCT Filed: Aug. 7, 1998

(86) PCT No.: PCT/EP98/05011

§ 371 (c)(1),
(2), (4) Date: Apr. 24, 2000

(87) PCT Pub. No.: WO99/07743

PCT Pub. Date: Feb. 18, 1999

(30) Foreign Application Priority Data

Aug. 8, 1997 (DE) ................. 197 34 370

(51) Int. Cl.
*C08B 30/00* (2006.01)
*C08B 30/08* (2006.01)

(52) U.S. Cl. .............. 127/1; 127/6; 127/7; 127/38; 536/124

(58) Field of Classification Search .......... 127/1, 127/6, 7, 9, 32–37, 65, 69–71; 536/124
See application file for complete search history.

(56) References Cited

U.S. PATENT DOCUMENTS

| | | | | |
|---|---|---|---|---|
| 3,446,664 A | * | 5/1969 | Komai | 127/28 |
| 4,221,609 A | * | 9/1980 | Hughes | 127/38 |
| 4,562,086 A | * | 12/1985 | Smolka et al. | 426/578 |
| 5,218,108 A | * | 6/1993 | Sommermeyer et al. | 536/111 |

FOREIGN PATENT DOCUMENTS

| | | |
|---|---|---|
| DE | 28 37 067 | 5/1979 |
| DE | 29 30 614 | 2/1980 |
| DE | 36 04 415 | 8/1987 |

OTHER PUBLICATIONS

CAS abstract of DE 2837067, 1979.*
CAS abstract of DE 360415, 1987.*
CAs abstract of DE 2930614, 1980.*

* cited by examiner

*Primary Examiner*—Leigh C. Maier
(74) *Attorney, Agent, or Firm*—Sturm & Fix LLP

(57) ABSTRACT

The invention relates to a method for the continuous production of hydrolytically broken down starch or hydrolytically broken down substituted starch products such as hydroxyethyl- or hydroxypropyl starch. The invention essentially consists of carrying out most of the hydrolytic breakdown in a pipe-shaped, temperature-controlled reactor having no mixing elements. The remaining breakdown is carried out in one or more reactors fitted with mixing elements (fine hydrolysis). The product obtained can be used both in the food industry and for medical purposes, especially as plasma diluent.

20 Claims, 1 Drawing Sheet

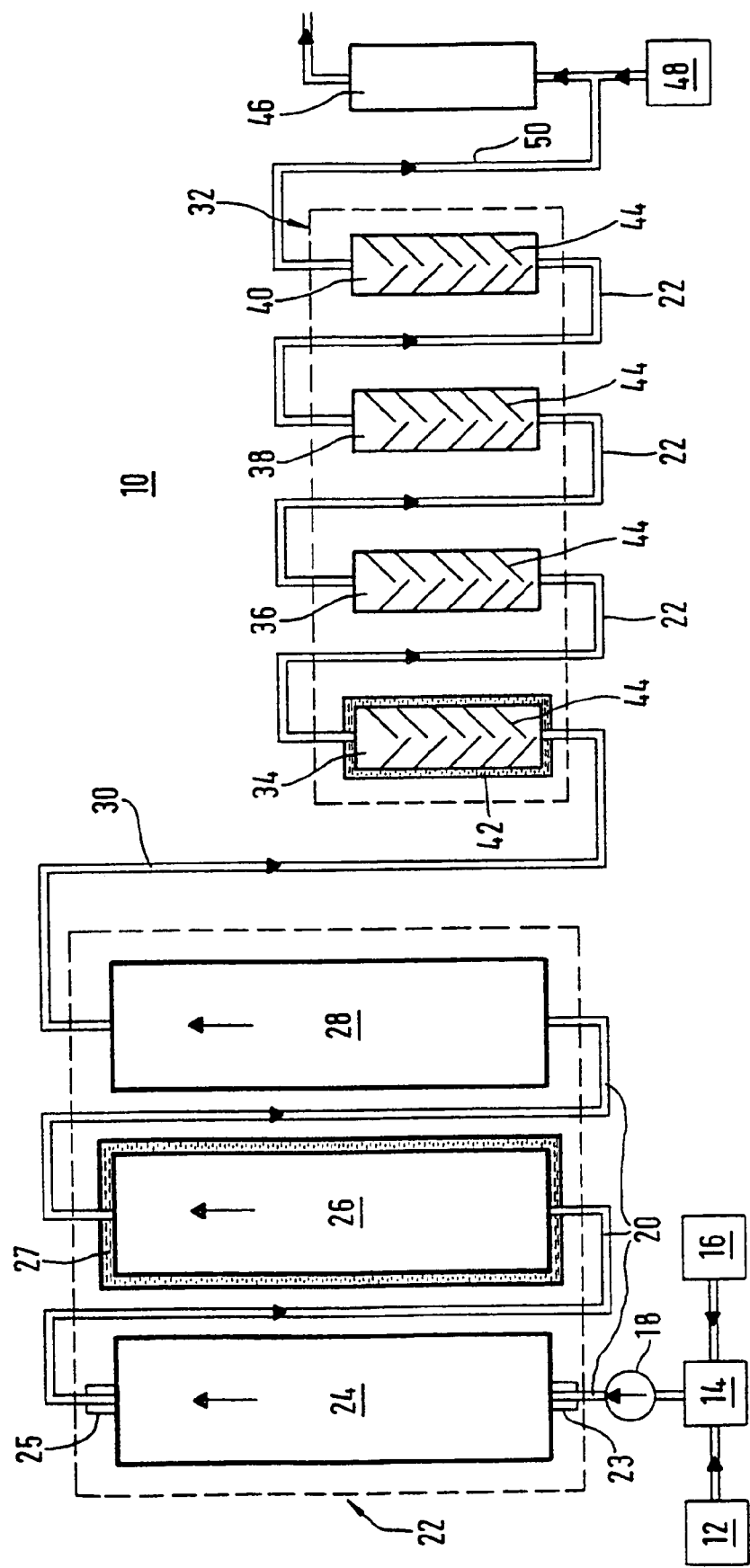

METHOD FOR THE CONTINUOUS PRODUCTION OF HYDROLYTICALLY BROKEN DOWN AND POSSIBLY SUBSTITUTED STARCH, USE OF HYDROLYTICALLY BROKEN DOWN STARCH AND DEVICE FOR PRODUCING SAME

Method for the continuous production of hydrolytically broken down starch or hydrolytically broken down substituted starch products.

The invention concerns a method for the production of hydrolytically broken down starch or hydrolytically broken down substituted starch products, such as hydroxyethyl starch or hydroxypropyl starch, use of the products produced according to the invention in the medical field, in particular as plasma diluent, as well as a device for producing hydrolytically broken down starch or hydrolytically broken down substituted starch products.

It is known to hydrolytically break down starch and substituted starch products, such as hydroxyethyl or hydroxypropyl starch. Thus, a method for producing a starch hydrolysate is described in DE-OS 30 000 465 in which α-amylase is used. The method described there works in a very complicated manner and can not easily be carried out in a continuous manner. Moreover, it can only be applied to a limited degree.

A method is also described in DE-A1 33 13 600 for the hydrolytical breakdown of starch in which α-amylase, beta-amylase or pullulanase is used, whereby the starch can be substituted, for example, with ethylene oxide before or after the hydrolysis.

The breakdown of hydroxyethyl starch to form a product that can be used as a plasma expander is described, inter alia, in EP-A1 0 402 724.

Transferring methods of this type to a continuous scale is not easily possible. Therefore, there is a need for a continuous method that works economically and that results in products that can be used in a variety of fields.

As is known, high demands are made on just those products which are used in the medical field. On the one hand, products are required that do not cause any allergies in the patient, on the other hand, the breakdown rate, i.e. the decrease in concentration within the first 24 hours, should be very high in the patient and the organ half-life short. Moreover, the clinical use of broken down starch products depends quite heavily on the physical chemical properties. In this connection, reference is made to the articles of Klaus Sommermeyer et al. that were published inter alia in Krankenhauspharmacie 8, (8271/8) (1987) and starch/Stärke 44 (5), 173–9 (1992).

The object of the invention is to provide a method for the continuous production of hydrolytically broken down starch or hydrolytically broken down substituted starch products that works economically, with which the properties of the breakdown products can be set selectively, carried out with slight apparatus-related and method-related assembly and which results in products that can be used especially in the medical field and in food technology.

This object is solved by a method according to the present invention. Further advantageous embodiments of the method according to the invention are described.

A further object of the invention is the use of the products produced according to a method as a plasma diluent or to produce dialysis solutions. A further object of the invention is a device for carrying out a method for the continuous production of hydrolytically broken down starch derivatives.

Brief Description of the Drawings

FIG. 1 is a schematic diagram illustrating the device for the continuous hydrolysis of starch or starch derivatives.

To carry out the method according to the invention, all kind of starches or starch derivatives that are soluble in the aqueous hydrolysis solution can be used. Such starches can be derived for example from potato starch, wheat starch, cassava starch and the like while the starches rich in amylopectin are especially suitable, such as the wax-like milo (SORGHUM) starch, corn starch or rice starch. The starch can also be used as an already partially broken down starch (a thin boiling starch). These starches have to be pre-treated or modified to be soluble in the aqueous hydrolysis solution. In particular, hydroxypropyl and preferably hydroxyethyl starches are used as modified starches.

In case the starch is already soluble in the aqueous hydrolysis solution the modification can be carried prior to hydrolysis, yet also after hydrolysis. Preferably, however, it is modified, especially ethoxylated, prior to hydrolysis.

The modified or non-modified starch to be broken down is advantageously used as an aqueous solution or suspension, whereby suspension is understood to also mean grains containing starch and found in water. The concentration of starch or modified starch in the solution or suspension can be adjusted within broad limits.

The concentration can already be set prior to hydrolysis with respect to the desired intended use of the end product: furthermore, it is possible to influence the property profile of the end product by selecting the concentration in combination with further parameters such as hydrolysis temperature, dwell time etc. Preferably, the concentration is 25–30% by weight relative to the total weight.

After mixing with a hydrolyzation agent, in particular a mineral acid such as hydrocholoric acid, it is heated or cooled to the desired temperature, preferably with the aid of heat exchangers.

The suspension or solution is then conveyed to a tubular tempered reactor, whereby reactor is understood to also be a plurality of reactor units which are arranged in tandem. The reactor is tempered to the desired hydrolysis temperature, preferably to 70–80° C. The product to be hydrolyzed is fed to the tubular reactor from the bottom i.e. against the force of gravity, so that the suspension or solution moves from the bottom to the top, i.e. in ascending direction. If several reactor units are used, all reactor units are aligned in parallel and are each flowed into from the bottom.

In principle, it is possible to carry out the predominant part of the hydrolysis in a single tube. However, several tubular reactor units can also be arranged in a row, for example, be arranged beside one another or above one another, as is preferred for production and handling reasons. The conveyance of the hydrolysis product from one reactor unit into the next reactor unit can be accomplished in a simple manner, e.g. with pipe connections, perhaps also by inserting an adjustable pump.

The tube reactors are laid out in such a manner or the flow velocity measured such that at least a predominant part of the hydrolysis, i.e. at least 60%, preferably 85–95% of the breakdown takes place in the tubular tempered reactors. Thus, this breakdown preferably takes place as a first step in the form of a rough breakdown—as will be described below. The tubular reactors preferably contain no mixing elements at all so as to ensure a uniform forward movement of the suspension during hydrolysis without mixing. Sampling points can be provided on the connecting pipes.

The product already broken down for the most part, e.g. up to 90%, can then be conveyed to one or more further reactors in which the hydrolytical breakdown is carried out to the desired extent (second step in the form of a fine breakdown). Preferably, the remainder of the hydrolysis in the fine breakdown step is carried out in reactors that have static mixing elements.

With aid of the reactor units, it is possible to conduct the hydrolysis up to a preset final value and to fine tune the method. Therefore, advantageously, these reactors are also provided with means for controlling the temperature. In this way, it is possible to accurately set the degree of hydrolysis. The degree of hydrolysis is preferably tested with aid of viscosity measurements.

According to the invention, it is preferable to carry out a two-step continuous breakdown process, consisting of a rough and fine breakdown. On the other hand, however, a a one-step breakdown method can also be carried out corresponding to the rough breakdown when the hydrolytic breakdown does not by necessity have to result in an exact preset degree of breakdown, but can fluctuate within set limits.

The flow of the liquid product to be hydrolyzed against the force of gravity has the advantage that the layers of the solution/suspension found in a reactor virtually do not mix. Due to the hydrolysis, amylolysis products having a decreasing chain length are continuously formed, the result of which is that the liquid layers have an ever lower viscosity, seen from the bottom of the reactor to the top. In the reactor, therefore, there are layers having a continuously decreasing drop in viscosity—seen from the bottom to the top against the force of gravity.

During hydrolysis, the solution to be treated is moved through the reactor at such a speed that enables an essentially undisturbed formation of this viscosity profile. After the reactor length, i.e. the reaction length during the continuous method, has been fixed, the conveying speed establishes the total reaction time which is determined in dependence on the selected degree of hydrolysis.

If a multiple tube reactor installation is used, then the connecting pipes are measured in such a way in their cross section that the layers having the same viscosity can flow from the one to the other reactor essentially without disturbance, i.e. without the layers mixing, so that the hydrolysis treatment can take place in the next reactor unit against the force of gravity.

The property profile of the hydrolysate obtained can also be influenced by the selection of the concentration of the initial solution or initial suspension as well as the molecular weight of the starch or starch derivative used, the degree of substitution, the hydrolysis temperature, the acid concentration and the like.

If modified broken down starch products are to be produced, then the starch is preferably modified prior to the hydrolysis. It is possible and preferable with the method of the invention to carry out the modification process and the hydrolysis process in a fully continuous manner.

In this way, starch, in particular broken down starch, can be mixed, for example, for ethoxylation with ethylene oxide, whereby so much caustic soda is added to the mixture that the desired pH is obtained. This pH is preferably in the base range and can e.g. have the value 13. The mixing and the reaction can be carried out continuously, whereby the conversion preferably takes place in one or more tube reactors connected in series and provided with static mixers. The ethoxylated product is then, as described above, mixed with hydrochloric acid for carrying out the hydrolysis and brought to the desired temperature and conveyed to the hydrolysis.

It was especially surprising that, with aid of the method according to the invention, it is possible to hydrolytically continuously break down starch and/or modified starch with a uniform profile in the end product. It was furthermore especially surprising that a hydrolysate having an advantageous molecular weight distribution is obtained in the tubular reactors without intermixing of the solution by means of static mixers or moving mixers, in particular that a very broad molecular weight spectrum is not produced due to the formation of channels, as was feared.

The method according to the invention offers a substantial simplification of the hydrolysis process and thus results in considerable savings in costs since only special steels (e.g. HASTELLOY) can be used for acid hydrolysis processes, which is quite expensive for equipment provided with static mixers.

It is possible to produce a hydrolysis product with specific properties in a selective and reproducible manner with the method of the invention. Thus, exactly defined final values such as molecular weight, molecular weight distribution, degree of substitution and the like can be set. These values can be constantly obtained in a reproducible manner for a long period, while in the so-called batch operation the fluctuations are very great and difficult to control. This not only applies to the breakdown of the starch, but also for the breakdown of modified products, so that, in combination with a modification process for the various intended purposes, it is possible to produce preparations having the desired properties.

The method is very fleixble and can be automated to a great extent.

The method according to the invention can be carried out with an installation as schematically shown in the drawing.

A device for the continuous hydrolysis of starch or starch derivatives is indicated with 10 in the drawing. A hydroxyethyl starch solution is continuously fed to a mixer/heat exchanger 14 from station 12, said mixer/heat exchanger 14 being connected with a container 16 that has e.g. hydrochloric acid as a hydrolyzation agent. A pH value is set at 1–2 in the mixer/heat exchanger 14 and the solution is tempered to a preselected hydrolysis temperature, e.g. 70–80° C.

The hydrolysis solution is then conveyed by means of a pump 18 having a preset pump rate, via a first conduit 20 to a reactor 22 (according to the drawing, three reactor units 24–28) as reaction stage (main or rough hydrolysis station) in such a way that the hydrolysis solution rises against the force of gravity from the bottom to the top, as is shown by the direction of the arrows in the reactor units 24–28. For this purpose, the reactor unit 24 has, when in operation, an inlet tube 23 arranged at the bottom and an outlet tube 25 arranged at the top. These tubes 23 and 25 are provided in the same way in the remaining reactor units 26 and 28. The conduit 20 is thereby dimensioned in such a way in its cross section that each of the hydrolysis layers arriving from the reactors 24–28 cannot essentially intermix.

On the other hand, however, it can also be sufficient that only one reactor unit 24 is used as main hydrolysis station (shown with 22 in a broken line), to the extent that it is adequately dimensioned in its volume. It is thereby essential to the invention that the slowly rising hydrolysis solution does not intermix in its layers, i.e. the individual layers with their various states of hydrolysis should not intermix, similar as the bases during fractionated distillation. As a result, a solution having a defined degree of hydrolysis can be drawn off in each case at the upper outlet point of the reactor units 24–28, whereby the hydrolysis can then be finely set. The reactor units 24–28 are therefore designated as main hydrolysis station. In particular, the reactor units 24–28 are not furnished with mixing elements on the inside which could cause the entire hydrolysis solution to be intermixed. Therefore, the hydrolysis gradient which is correlated with the viscosity of the individual layers should remain essentially unchanged, i.e. the individual layers should not mix with one another.

Advantageously, the reactor units 24–28 have a tempering jacket 27 as shown symbolically in the reactor unit 26 in the drawing. This tempering jacket is flowed through by a tempering liquid, usually water, maintained at a preset temperature and thus maintains the contents of the respective reactor units 24–28 at the desired temperature. The latter is determined in each case thereby that liquid samples are removed at specific points on the reactor units 24–28 to determine the respective viscosity, i.e. the respective degree of hydrolysis, and that the final degree of hydrolysis is determined herefrom with reference to tables and the known conveying rate.

The reactor units 24–28 are dimensioned in such a way that a minimum flow rate is ensured at a preset viscosity to prevent an intermixing of the respective layers due to diffusion. The latter essentially depends inter alia on the viscosity. Thus, the lower limit of the flow rate is at about 3 cm/min, if the viscosity of the solution to be hydrolyzed is at about 20 mPa×s. Advantageously, the flow rate is between 5–20, especially between 10–15 cm/min.

The length/diameter ratio of the reactor units 24–28 is also determined by the throughput of the solution to be hydrolyzed. Advantageously, this ratio is between 10:1 to 20:1.

Advantageously, the main hydrolysis station 22 is connected with a fine hydrolysis station 32 (shown by a broken line) by means of a second conduit 30, as shown by the reactor units 34–40. These reactor units 34–40 are advantageously connected with a tempering unit 42, for example, by a tempering jacket, through which a tempering liquid flows that is maintained at a preset temperature and which corresponds to the tempering jacket 27. The temperature that is advantageous for the hydrolysis can be set herewith, said temperature being advantageously monitored and controlled by means of the viscosity setting in in the hydrolysis solution. Moreover, these reactor units 34–40 are furnished with mixing elements 44 (shown schematically) so that a uniform intermixing takes place in the reactors to ensure a uniform hydrolysis. The tempering unit 42 is only shown in the drawing in connection with the reactor unit 34 and can, of course, also be provided in the other reactor units 36–40. Similarly, it is fed from a standard tempering liquid source (not shown).

For example, a hydrolysis of up to 95% can take palce in the main hydrolysis station 22, while only 5% of the desired degree of hydrolysis are obtained in the fine hydrolysis station 32.

As noted above, according to the invention, the fine hydrolysis station 32 does not have to be provided, since a hydrolysis product having a dense molecular weight distribution is produced there. If a dense distribution of this type is not required, then a fine hydrolysis station 32 of this type can be omitted.

As shown in the drawing, the liquid to be hydrolyzed is advantageously also conveyed from the bottom to the top in the fine hydrolysis station 32 in order to substantially eliminate the effects of the force of gravity.

To stop the hydrolysis, the solution is mixed with a caustic soda, conveyed from the storage vessel 48, in a neutralization station 46 at the end of the hydrolysis. In this respect, the container 46 is connected to the fine hydrolysis station 32 with a third conduit 50.

The mixture is then conveyed for further treatment, e.g. diafiltration and spray drying, from the vessel 46 to further treatment apparatus (not shown).

The invention will be explained in further detail by the following example.

EXAMPLE 1

A 30% starch solution is produced by adding water and lye. Hydroxylethyl starch having a molecular weight of 1.4 million daltons is produced therefrom in a continuous starch ethoxylating installation by menas of ethylene oxide and conveyed to a tube reactor without mixing elements at a volume flow of about 11.3 l/h. The reactor is dimensioned about 2.6 m×DN 100. The ethoxylation is not an object of the invention since a starch can also be used for the subsequent hydrolysis.

0.2 l/h 25% HCl is added to the hydroxyethyl starch solution in doses prior to being introduced into a hydrolysis reactor; furthermore, the reaction solution is brought to a temperature of 70° C. by means of a heat exchanger, whereby the pH value is brought to about 1.0. The hydrolysis reactor is maintained at 70° C. by means of tempering, whereby it is essential that the untreated solution flow through the reactor, which does not have mixing elements, from the bottom to the top (against the force of gravity). The dwell time of the solution is approximately 2 hours. The molecular weight was thereby reduced from 1.4 million to 300,000 daltons.

In a fine hydrolysis part, advantageously connected in tandem and consisting of several reactors having static mixing elements, a final molecular weight (weight means) of approximately 250,000 daltons is set. The hydrolysis is then ended by means of neutralization. The mixture is then purified by means of diafiltration with aid of a membrane to an exclusion limit of 50,000 daltons. The dried product is extremely suitable as a plasma diluent.

The invention claimed is:

1. Method for the continuous production of a plasma diluent or dialysis solutions based on hydrolytically broken down starch derivatives that are optionally substituted, by hydrolyzing with a hydrolysis agent in an aqueous medium and subsequent neutralization to stop the hydrolysis, the method comprising:
   a main hydrolysis wherein an aqueous solution that contains the starch or optionally substituted starch to be hydrolyzed is continuously conveyed through at least one reactor essentially free of mixing against the force of gravity in the hydrolysis step at a flow rate of about 5 to 20 cm/min; and
   a fine hydrolysis, wherein the fine hydrolysis is carried out after the main hydrolysis, a roughly hydrolyzed starch solution being fed to a tubular reactor with mixing elements at a preset temperature during said fine hydrolysis.

2. Method according to claim 1, wherein the at least one reactor has at least one tubular reactor that has an inlet tube disposed at the bottom and an outlet tube disposed at the top when in the operative state.

3. Method according to claim 1, wherein tubular reactors are arranged essentially vertically when in operation and starch or optionally substituted starch to be hydrolyzed is conveyed from the bottom from the top.

4. Method according to claim 1, wherein the reactor(s) are tubular reactor(s) that are tempered at a preset temperature of 25 to 100° C.

5. Method according to claim 1, wherein main hydrolysis is carried out in a tubular tempered reactor for up to 85 to 95%.

6. Method according to claim 1, wherein etherified starch is used.

7. Method according to claim 1, wherein the fine hydrolysis is carried out with several reactors provided with static mixing elements.

8. Method according to claim 1, wherein thin boiling starch is ethoxylated continuously with ethylene oxide in a base environment, the ethoxylated product is acidified with mineral acid, the main hydrolysis is carried out at a reaction temperature of 60 to 100° C. and the hydrolysis is terminated by neutralization with lye and cooling.

9. Device for carrying out the method according to claim 1 including a feeding device for starch solution, a container for a hydrolyzing agent, a mixing and heating station for mixing the aqueous starch solution with the hydrolyzing agent and heating the mixture to a preset temperature, and a pump for feeding the mixture into at least one reactor, whereby the reactor, when in use, is arranged essentially vertically and has an inlet tube at the bottom and an outlet tube at the top and the pump is operated in such a way that it continuously feeds the aqueous starch solution to the inlet tube at the bottom at a preset pump rate, so that the aqueous starch solution is conveyed through the reactor to the outlet tube against the force of gravity; and wherein a fine hydrolysis station in the form of at least one reactor unit is connected in tandem after the reactor as a main hydrolysis station, each of said reactor units having mixing elements.

10. Device according to claim 9, wherein the reactors are each provided with a tempering unit.

11. Method according to claim 2 further comprising a fine hydrolysis, wherein a fine hydrolysis is carried out after the main hydrolysis, the roughly hydrolyzed starch solution being fed to a tubular reactor with mixing elements at a preset temperature during said fine hydrolysis.

12. Method according to claim 2, wherein the tubular reactors are arranged essentially vertically when in operation and product to be hydrolyzed is conveyed from the bottom to the top.

13. Method according to claim 1, wherein the tubular reactors are arranged essentially vertically when in operation and starch or optionally substituted starch to be hydrolyzed is conveyed from the bottom to the top.

14. Method according to claim 2, wherein the tubular reactors are tempered at a preset temperature of 25 to 100° C.

15. Method according to claim 1, wherein the tubular reactors are tempered at a preset temperature of 25 to 100° C.

16. Method according to claim 3, wherein the tubular reactors are tempered at a preset temperature of 25 to 100° C.

17. Method according to claim 1, wherein main hydrolysis is carried out in the tubular tempered reactor for up to 85 to 95%.

18. Method according to claim 6 wherein the etherified starch is wax cornstarch.

19. Method according to claim 6 wherein a starch etherified with at least one of ethylene oxide and propylene oxide is used.

20. Method for the continuous production of a plasma diluent or dialysis solutions based on hydrolytically broken down starch derivatives that are optionally substituted, by hydrolyzing with a hydrolysis agent in an aqueous medium and subsequent neutralization to stop the hydrolysis, the method comprising:

a main hydrolysis providing a roughly hydrolyzed starch solution where starch breakdown ranges from about 60% to about 95%, wherein an aqueous solution that contains the starch or optionally substituted starch to be hydrolyzed is continuously conveyed through at least one reactor essentially free of mixing against the force of gravity in the hydrolysis step at a flow rate of about 5 to 20 cm/min; and a fine hydrolysis providing further starch breakdown, wherein the fine hydrolysis is carried out after the main hydrolysis, the roughly hydrolyzed starch solution being fed to a tubular reactor with mixing elements at a preset temperature during said fine hydrolysis.

* * * * *